United States Patent [19]
Green

[11] 3,949,924
[45] Apr. 13, 1976

[54] SURGICAL STAPLING INSTRUMENT
[75] Inventor: David Thomas Green, Norwalk, Conn.
[73] Assignee: United States Surgical Corporation, New York, N.Y.
[22] Filed: Oct. 18, 1974
[21] Appl. No.: 516,111

[52] U.S. Cl................................. 227/132; 227/19
[51] Int. Cl.² .......................................... B25C 5/02
[58] Field of Search...................... 227/19, 132, 146

[56] References Cited
UNITED STATES PATENTS

| | | | |
|---|---|---|---|
| 2,137,642 | 11/1938 | Cavanagh | 227/132 |
| 2,320,568 | 6/1943 | Cavanagh | 227/132 X |
| 2,765,463 | 10/1956 | DeAnguera | 227/132 X |
| 3,819,100 | 6/1974 | Noiles et al. | 227/19 |

Primary Examiner—Granville Y. Custer, Jr.
Attorney, Agent, or Firm—Fleit & Jacobson

[57] ABSTRACT

A surgical stapling instrument for applying sterilized staples to the disunited skin or fascia of a patient in order to effect a joining of the skin or fascia. The instrument is adapted to associate with a staple-carrying cartridge having a plurality of staples therein. The instrument is manually powered and includes an impact mechanism for forming the staples. A nose portion is rotatably mounted in a hand-held main body portion and adapted to mount the staple-carrying cartridge so that the stapling angle can be varied without rotating the hand-held portion of the stapler. A clutch means is provided for ensuring that the staple-advancing drive means of the instrument is only activated once per stapling operation.

14 Claims, 8 Drawing Figures

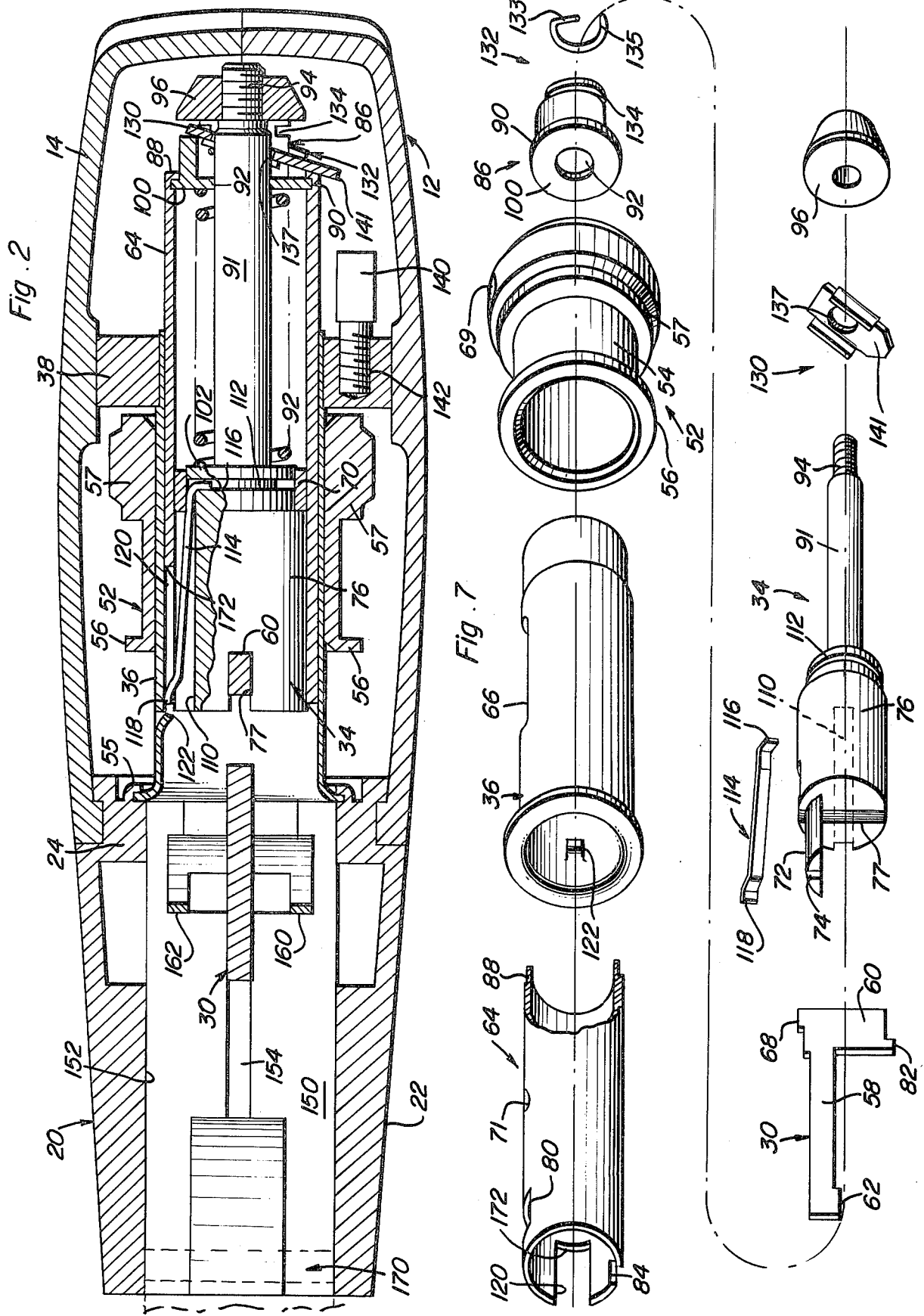

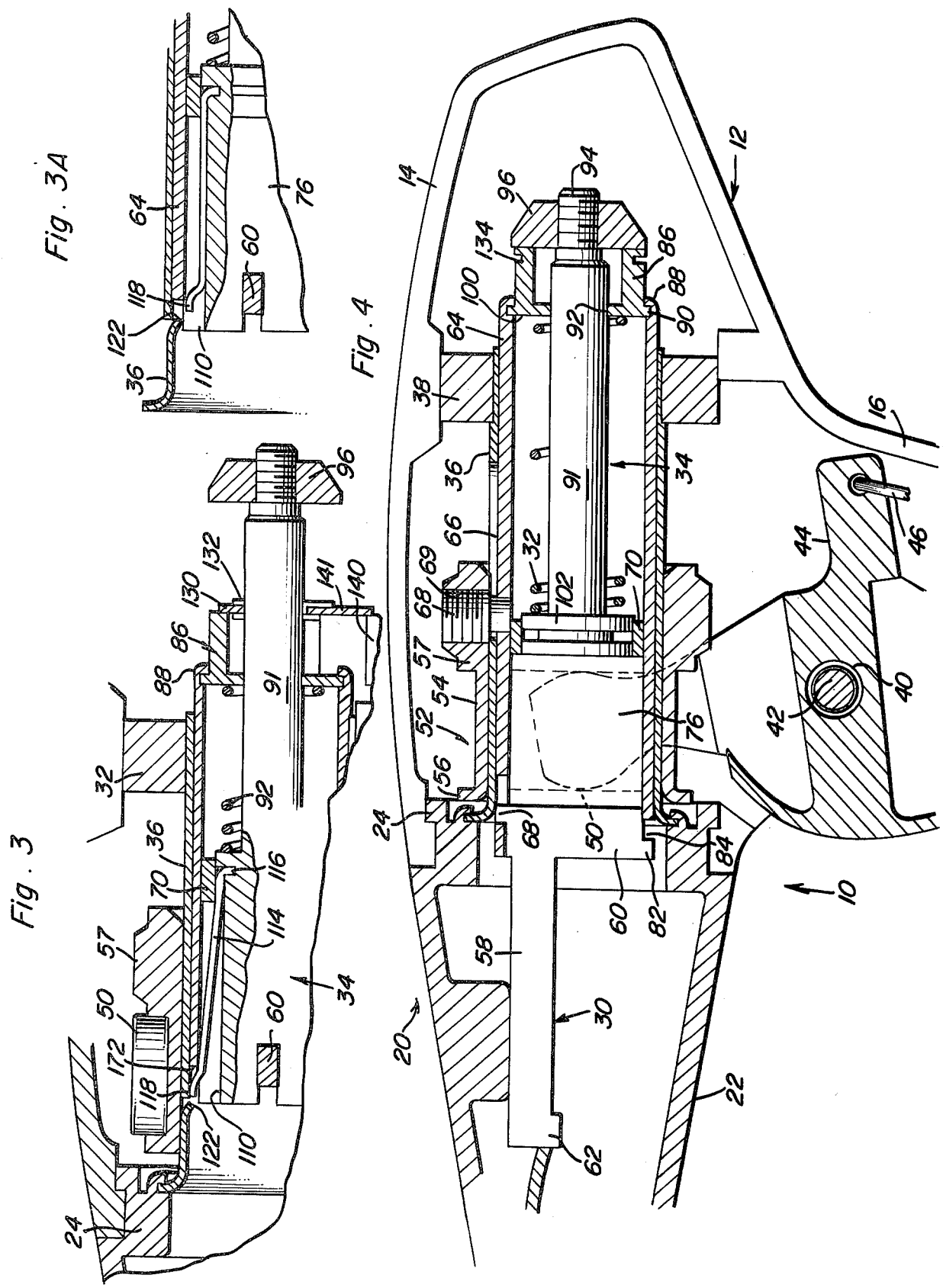

SURGICAL STAPLING INSTRUMENT

BACKGROUND OF THE INVENTION

In U.S. Pat. No. 3,643,851, assigned to the present assignee and entitled SKIN STAPLER, there is disclosed a surgical stapler for joining the disunited skin of a patient. The surgical stapler disclosed in this commonly assigned patent employs a staple-carrying cartridge comprising an anvil adapted to lie flush with the skin, a plurality of staples which are to be folded around the anvil, and a pusher for ejecting and bending the staples around the anvil. The surgical stapling instrument adapted to accept the staple-carrying cartridge in this commonly assigned patent is powered by a pressurized gas. Later developments of the gas-powered stapler and cartridges for applying surgical staples to external skin and internal fascia are disclosed in U.S. Pat. No. 3,662,939, assigned to the present assignee and entitled SURGICAL STAPLER FOR SKIN AND FASCIA.

Although these gas-powered instruments represent a marked advance over the state-of-the-art, there are certain disadvantages associated with the use of gas-powered units of this type. One of the obvious disadvantages is the necessity for replacing the gas cartridges after their contents have been exhausted, and a second is the inconvenience associated with storing and maintaining a supply of these cartridges. Also, the powering mechanism is complex, is hence somewhat costly, and comprises numerous close-tolerance elements which tend to be susceptible to malfunction. For these and other obvious reasons, it would be advantageous to have a simple surgical stapling instrument adapted to accept staple-carrying cartridges, but which is powered manually and without the intervention of a gaseous medium and the disadvantages associated therewith.

A manually powered surgical stapling instrument adapted to accept staple-carrying cartridges of the type disclosed in the above commonly assigned patents is disclosed in U.S. Pat. No. 3,819,100, assigned to the present assignee and entitled SURGICAL STAPLING INSTRUMENT. The surgical stapling instrument generally comprises a pusher-activating means for driving the pusher element of the staple-carrying cartridge to eject and form the staples around the anvil means of the cartridge including a thrust bar slidably mounted for reciprocative movement in the nose portion of the stapler. The surgical stapling instrument also comprises drive means to activate the staple-advancing means in the staple-carrying cartridge for driving the staples toward the anvil including pinion gears and pinion shafts also housed within the nose portion of the stapler.

Recently, cartridges have been designed which eliminate the requirement for the complex gearing once needed in the powering of the instrument. With these cartridges, the output shaft of the powering instrument need only have rectilinear thrust capabilities. The staples are advanced by means designed into the cartridges themselves. In commonly assigned U.S. Pat. No. 3,618,842 entitled SURGICAL STAPLING CARTRIDGE WITH CYLINDRICAL DRIVING CAMS, the advancing pusher, integral with the cartridge, rotates a pair of staple-driving screws by means of cams formed in the rear portions of the screws. In commonly assigned U.S. Pat. No. 3,638,847 entitled RACHET DRIVEN CARTRIDGE FOR SURGICAL INSTRUMENTS, the staples are driven forward by the interaction of pairs of opposing ratchet teeth integral with the cartridge. Finally, in commonly assigned U.S. Pat. No. 3,717,294 entitled CARTRIDGE AND POWERING INSTRUMENT FOR STAPLING SKIN AND FASCIA, a flexible toothed belt is moveably housed in a main body. Staples are guided and advanced by association with spaced teeth of the flexible belt. The cartridge is equipped with an anvil integral with the main body and a pusher which serves the functions of advancing the staples and singly ejecting and forming the same.

Accordingly, it is a broad object of the present invention to provide a surgical stapling instrument for stapling the disunited skin or fascia of a patient which is manually powered and wholly operated by mechanical means.

It is another object of the present invention to provide a surgical stapling instrument which is adapted to associate with a cartridge requiring only rectilinear thrust capability.

It is still another object of the present invention to provide a surgical stapling instrument which is uniform and smooth to operate and which consistently forms the staples with the same mechanical force.

It is yet another object of the present invention to provide a surgical stapler in which the staple-carrying cartridge is mounted so that it is rotatable relative to the hand-held main body portion of the instrument so that the staples can be applied at any angle without the necessity for rotating the hand-held portion of the instrument.

Another object of the present invention is to provide a surgical stapler with means for ensuring that the staple-advancing drive means of the instrument is activated only once in each stapling operation.

These and other objects of the invention, as well as many of the attendant advantages thereof, will become more readily apparent when reference is made to the following description taken in conjunction with the accompanying drawings.

SUMMARY OF THE INVENTION

The present invention relates to a surgical instrument for stapling together disunited segments of the external skin or internal fascia of a patient.

The surgical stapling instrument generally comprises a main body portion having a nose portion rotatably mounted therein and adapted to receive and mount a staple-carrying cartridge. The nose portion of the stapler has the drive means for advancing and forming the staples mounted thereto. A pusher-activating means for driving the pusher element of the staple-carrying cartridge to advance, eject and form the staples around the anvil means of the cartridge comprises a thrust bar slidably mounted for reciprocative movement in the stapler. The thrust bar is adapted to move with a collar element slidably mounted in the stapler. A trigger means comprises a handle which is pivotally mounted on the main body portion of the stapler and has means for engaging the collar element so that the thrust bar is moved forward by squeezing the trigger to advance the staples.

An impact mechanism mounted in the stapler includes an impact spring which is loaded by squeezing the trigger and a plunger acted upon by the impact spring which is released and strikes the thrust bar when the staples are ready for ejection and forming. A return spring attached to the trigger and to the main body portion of the stapler functions to return the thrust bar to its initial position after the thrust stroke of the bar has been completed. Means are also provided for preventing more than one staple from being placed in the ready position of the staple-carrying cartridge during the stapling operation. This means comprises a clutch means which prevents the return of the thrust bar to its initial position until it has completed a full stroke, thereby ejecting a staple from the staple-carrying cartridge.

BRIEF DESCRIPTION OF THE DRAWINGS

FIG. 2 is a horizontal cross-section taken along line 2—2 of FIG. 1;

FIG. 3 is similar to FIG. 2 but shows the stapler during the stapling operation after the staples have been advanced;

FIG. 3A is similar to FIG. 3 but shows the latch spring being cammed away from its abutment;

FIG. 4 is similar to FIG. 1 but shows a portion of the stapler during the stapling operation after the plunger has been released and impacted the thrust bar;

FIG. 7 is an exploded, perspective view of the staple advancing, ejecting and forming means of the surgical stapling instrument.

DETAIL DESCRIPTION OF THE INVENTION

Figure 1:
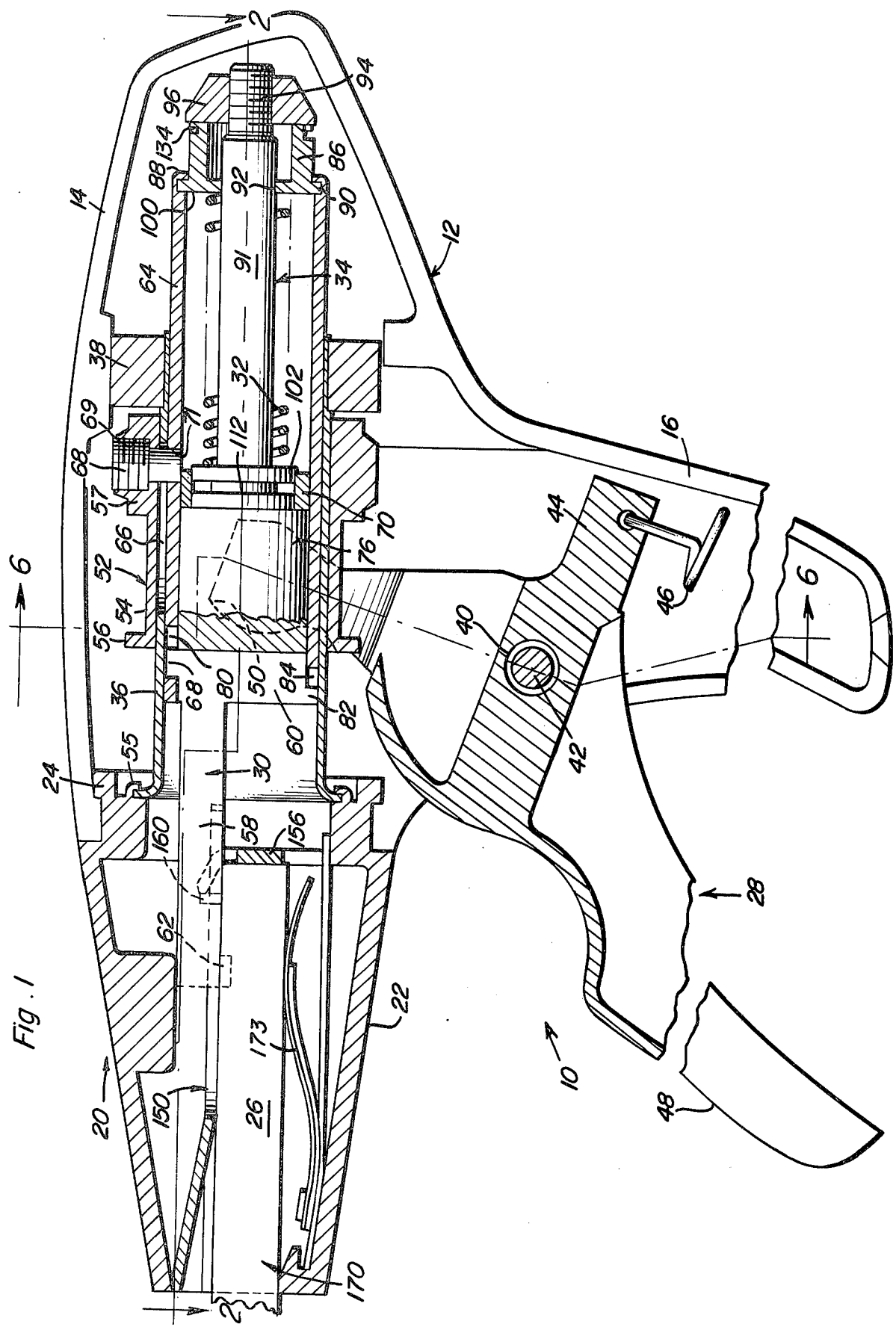
FIG. 1 is a vertical cross-section of the surgical stapling instrument of the present invention.

The surgical stapler of the present invention will first be described in general terms. The stapler shown generally at 10 comprises housing 12 having main body portion 14 and handle portion 16. Nose portion 20 of the stapler 10 is rotatably mounted in main body portion 14 of housing 12. Nose portion 20 includes a front section 22 extending out of housing 12 and adapted to mount staple-carrying cartridge 26. Nose portion 20 further includes a rear section 24 located inside housing 12 and acting to mount the driving means for advancing, ejecting and forming staples from the staple-carryiing cartridge. Staple-carrying cartridge 26 is partially shown fitted into nose portion 20 of stapler 10 in FIG. 1.

The staples in staple-carrying cartridge 26 are advanced, ejected and formed by mechanical means only and without the intervention of a gaseous medium. Accordingly, the power for advancing, ejecting and forming the staples in cartridge 26 comes from the manipulative force supplied to stapler 10 by the surgeon. This force is transmitted to the drive means of stapler 10 by means of trigger 28 which generally comprises a handle pivotally attached to housing 12. Pivoting of trigger 28 causes a thrust bar 30, the pusher-activating means, to drive the pusher element of staple-carrying cartridge 26 forward to advance the staples. At the same time, impact spring 32 is loaded by pivoting of trigger 28 and then plunger 34 acted upon by impact spring 32 is released and strikes thrust bar 30 to eject and form a staple.

Figure 6:
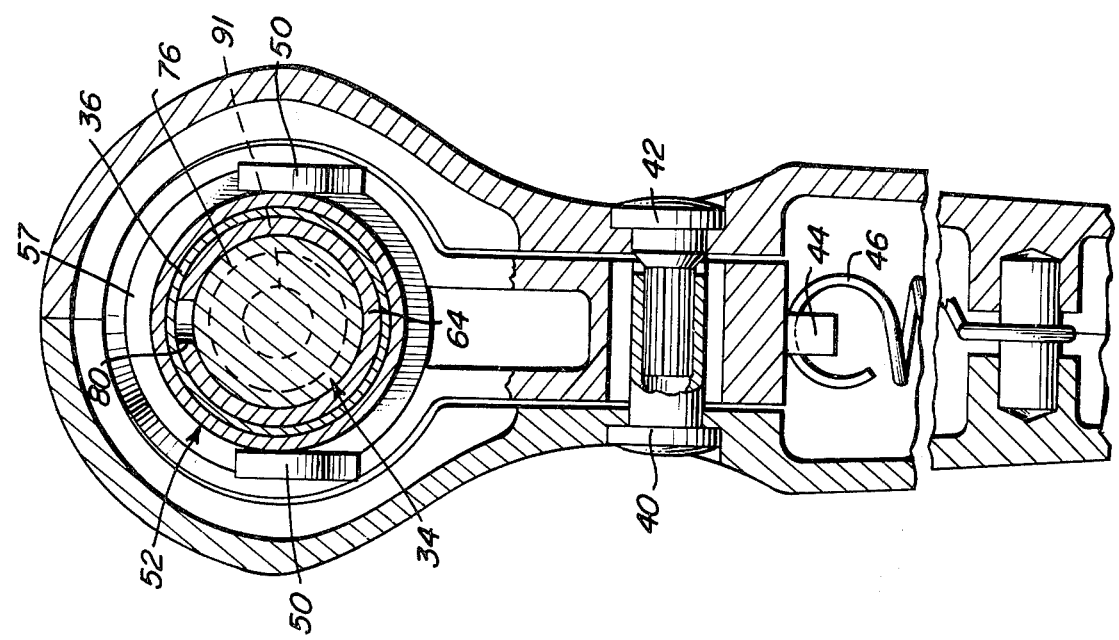
FIG. 6 is a vertical cross-section of the stapler looking rearwardly.
Figure 5:
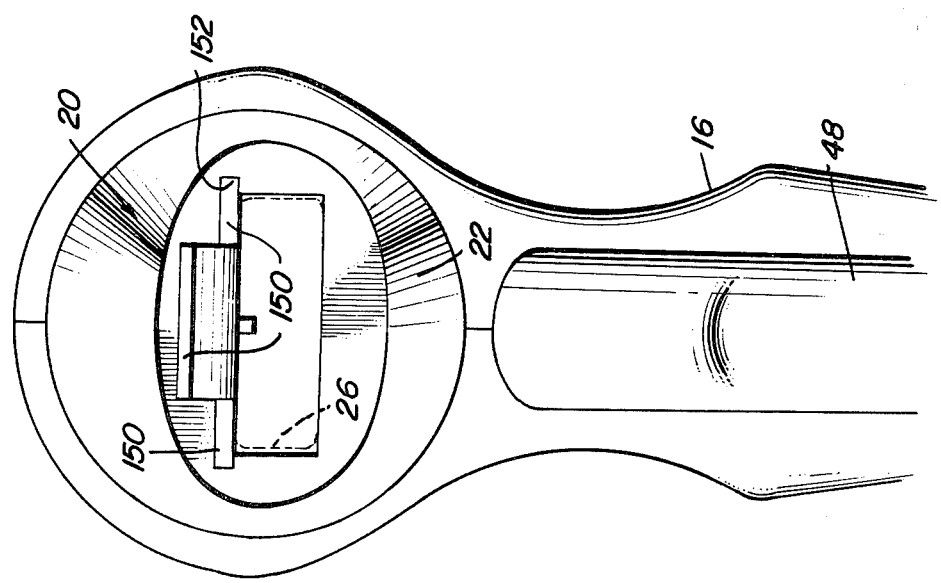
FIG. 5 is a front view of the stapler with the staple-carrying cartridge mounted and ready for use.

With reference now to FIGS. 1 and 6, trigger 28 will be described. Trigger 28 is pivotally mounted to housing 12 by means of stud 40 and drive pin 42. Trigger 28 is of appropriate size and shape to be conveniently gripped by the operating hand of a surgeon. The trigger includes a rearward extending portion 44 to which is attached one end of a return spring 46. The other end of return spring 46 is attached to housing 12 and functions to return trigger 28 and thrust bar 30 to their initial positions after staple forming has occurred. Trigger 28 is of Y-shape and includes a lower hand-engaging portion 48 and and upper force-transmitting yoke portion 50.

Yoke 50 embraces a collar 52 slidingly mounted around the mid-section of support tube 36. Support tube 36 is mounted at its forward end to the rear section 24 of nose portion 20 and is adapted to rotate therewith. The rearward end of support tube 36 is rotatably mounted to main body portion 14 by support bushing 38. Collar 52 includes a cylindrically-shaped body member 54 having outwardly and radially extending flange portions 56 and 57 at each end. Yoke 50 is positioned around cylindrically-shaped body member 54 and between the flange portions 56 and 57. Shoulder portion 55 of nose portion 20 limits the forward movement of collar 52. Pivoting of trigger 28 results in longitudinally directed force being exerted on collar 52 by yoke portion 50 of trigger 28. Accordingly, when the trigger is activated, collar 52 simultaneously slides along the mid-section of support tube 36. Also, by this arrangement, collar 52 is free to rotate relative to trigger 28.

With reference to FIGS. 1 and 7, thrust tube 64 is slidingly mounted in support tube 36. Support tube 36 has longitudinally extending slot 66 formed therein through which thrust stud 68 extends. Thrust stud 68 is mounted in bore 69 in collar 52 and extends into an opening 71 in thrust tube 64. Thrust stud 68 connects collar 52 to thrust tube 64 so that the two elements move together. Slot 66 permits collar 52 and thrust tube 64 to move together longitudinally relative to support tube 36. On the other hand, with this arrangement, collar 52 and thrust tube 64 rotate with support tube 36 when nose portion 20 is rotated. Plunger 34 is slidingly mounted in thrust tube 64 by means of retainer bushing 70. The forward end of plunger 34 comprises nose portion 72 having a longitudinally extending slot 74 formed therein. Main body portion 76 of plunger 34 also has a longitudinally extending slot 77 formed therein which is aligned with slot 74.

Thrust bar 30 includes an elongated central section 58 having a rear portion 60 which extends into slots 74 and 77 in plunger 34. A pusher-engaging extension 62 is positioned at the forwardmost end of thrust bar 30. Thrust bar 30 is slidingly mounted in the stapler and is adapted to rotate with nose portion 20. Thrust bar 30 is adapted to move with collar 52 by means of its attachment to thrust tube 64. More specifically, rear portion 60 of thrust bar 30 includes upper extension 68 which extends into a slot 80 in thrust tube 64 and lower extension 82 which extends into slot 84 in thrust tube 64. Accordingly, thrust bar 30 reciprocates back and forth with collar 52 when trigger 28 is pivoted, and thrust bar 30 rotates with collar 52 when nose portion 20 is rotated.

The rearwardmost end 88 of thrust tube 64 is closed by clutch retainer 86. More specifically, the rearwardmost end 88 of thrust tube 64 is peened over flange 90 at the forwardmost end of clutch retainer 86. The rearwardmost end of plunger 34 comprises a shaft 91 which extends through opening 92 in clutch retainer 86. The rearwardmost end of shaft 91 is threaded at 94 to receive cap 96. Impact spring 32 is positioned around shaft 91 of plunger 34 and acts between shoulder 100 on the forwardmost end of clutch retainer 86 and shoulder 102 on the rearwardmost end of main body portion 76 of plunger 34.

The main body portion 76 of plunger 34 has a longitudinally extending slot 110 formed in its side wall. Main body portion 76 also has an annular slot 112 formed at its rearwardmost end. A latch spring 114 is housed in longitudinally extending slot 110 and has one inturned end 116 extending into annular slot 112. End 116 is retained in annual slot 112 by retainer bushing 70. The other end 118 of latch spring 114 is positioned at the forwardmost end of main body portion 76 of plunger 34 and is turned slightly outward so that it extends through a slot 120 in thrust tube 64 and rides against the inner wall of support tube 36. End 118 of latch spring 114 is positioned to abut abutment 122 on support tube 36 momentarily after trigger 28 is squeezed.

Mounted on clutch retainer 86 is clutch plate 130. Clutch plate 130 is retained on clutch retainer 86 by hair spring clutch 132 which has a leg 133 engaged in annular groove 134 at the rearwardmost end of clutch retainer 86 and a second offset leg 135 abuting the rearwardmost end of clutch plate 130. In the position of clutch plate 130 shown in FIG. 2, thrust tube 64 is permitted to move to the left or toward nose portion 20 of stapler 10. However, movement to the right or rearward end of main body portion 14 of housing 12 is not permitted after thrust tube 64 has advanced toward nose portion 20 because clutch plate 130 will lock against the shaft 91 of plunger 34 which extends through opening 137 in clutch plate 130. The means for unlocking clutch plate 130 comprises clutch release stud 140 which is mounted in bore 142 in support bushing 38. As seen in FIG. 3, clutch release stud 140 contacts extension 141 of clutch plate 130 and moves clutch plate 130 into a vertical position when thrust tube 64 has advanced to its forwardmost position allowing thrust tube 64 and plunger 34 to be moved to their rest positions.

FIG. 2 shows a top view of locator plate 150 with thrust bar 30 in its initial position. Locator plate 150 is housed in opening 152 in the forward end 22 of nose portion 20. Locator plate 150 has a longitudinally extending slot 154 which receives pusher-engaging extension 62 of thrust bar 30 and thereby allows thrust bar 30 to reciprocate. Locator plate 150 also includes downwardly extending portion 156 against which abuts the rearwardmost end of cartridge 26.

With reference now to FIG. 1, the association of the staple-carrying cartridge 26 with the stapler 10 will be explained. Staple-carrying cartridge 26 is detachable mounted on nose portion 20. Staple-carrying cartridge 26 is elongated and has a pair of upwardly extending spaced tabs 160 at its rear end. The spacing between tabs 160 is sufficient to allow pusher-engaging extension 62 to freely slide therebetween and tabs 160 are dimensioned so as to fit into slots 162 near the rearwardmost end of locator plate 150. Therefore, when tabs 160 are properly positioned, staple-carrying cartridge 26 cannot be inadvertently pulled out of nose portion 20 of stapler 10, and cartridge 26 is fixed against forward movement during the stapling operation.

Staple-carrying cartridge 26 is mounted in stapler 10 by inserting the end of cartridge 26 into opening 170 in nose portion 20. The rearward end of staple-carrying cartridge 26 engages a leaf spring 173 which urges the cartridge 26 upwardly until tabs 160 are positively locked into their associated openings 162 in locator plate 150. With cartridge 26 in this position, pusher-engaging portion 62 is located in longitudinally extending slot 154 of locator plate 150 and is engaged with the staple actuating member of cartridge 26. The cartridge 26 is removed from the stapler 10, when exhausted of staples, by reversing the insertion steps.

In operation, a staple-carrying cartridge 26 is inserted into stapler 10 as described above and then trigger 28 is gripped and squeezed by the operating hand of the surgeon. This causes upper force-transmitting yoke portion 50 to slide collar 52 and thrust tube 64 forward along the mid-section of support tube 36. At the same time, thrust bar 30 is caused to move forward thereby advancing the staples in cartridge 26. Plunger 34 is prevented from moving forward as soon as end 118 of latch spring 114 abuts abutment 122 on support tube 36. Continued squeezing of trigger 28 causes collar 52 and support tube 36 to take the position shown in FIG. 3. At this point, spring 32 is essentially fully loaded by being compressed between shoulder 100 of clutch retainer 86 and shoulder 102 of main body portion 76 of plunger 34. In this position, camming surface 172 which comprises the base of slot 120 in thrust tube 64 is positioned adjacent to the end 118 of latch spring 114. During the movement of thrust bar 30 from the rest position shown in FIGS. 1 and 2 to the position shown in FIG. 3, thrust bar 30 has caused the staples to be advanced into the ready position in cartridge 26. In other words, a staple is ready to be ejected and formed around the anvil of cartridge 26. Also, it will be noted from FIG. 3, as pointed out above, that clutch plate 130 has been moved into a vertical position by clutch release stud 140

Further squeezing of trigger 28 causes camming surface 172 to cam end 118 of latch spring 114 out of engagement with abutment 122 as shown in FIG. 3A. This releases plunger 34 and causes plunger 34 to impact thrust bar 30 under the influence of impact spring 32 thereby ejecting and forming a staple around the anvil of cartridge 26. At this point, the staple has been applied to the disunited skin or fascia of the patient. Thereafter, return spring 46 pivots trigger 28 in the clockwise direction and yoke 50 forces collar 52 and thrust tube 64 back to their original rest position shown in FIGS. 1 and 2. At the same time, plunger 34 is moved to its rest position by clutch retainer 86 acting upon cap 96. After plunger 34 returns to its rest position, hair spring clutch 132 forces clutch plate 130 back in engagement with thrust tube 64 as shown in FIG. 2. Also, during the return movement, end 118 of latch spring 114 is cammed inwardly by abutment 122 of support tube 36 and then springs back into its original position touching the inner wall of support tube 36 as shown in FIG. 2.

Above there has been described a specific embodiment of the present invention. It should be noted, however, that the above description was given for illustrative purposes only and that many alterations and modifications may be practiced by those skilled in the art without departing from the spirit or the scope of the present invention. It is the intent therefore that the present invention not be limited to the above but be limited only as defined in the appended claims.

I claim:

1. A manually powered surgical stapling instrument for applying sterilized staples to the disunited skin or fascia of a patient for affecting a joining of the skin or fascia, the instrument adapted to associate with a staple-carrying cartridge having anvil means at one end thereof and adapted to house a plurality of staples therein, a pusher element slidably mounted therein for advancing said staples in said cartridge, for ejecting said staples from said cartridge and for forming said staples around said anvil means, said surgical stapling instrument comprising: a main body portion; means for mounting said staple-carrying cartridge on said main body portion; pusher-activating means mounted to reciprocate in said main body portion for driving said pusher element forward to advance, eject and form said staples; trigger means for transmitting a manually applied force to said pusher-activating means to advance said pusher-activating means and thereby advance said staples; and impact means powered by said trigger means for impacting said pusher-activating means after said pusher-activating means is advanced by said manually applied force to further advance said pusher-activating means and thereby eject and form said staples.

2. The instrument defined in claim 1, wherein said impact means comprises an impact spring, a plunger acted upon by said impact spring, means for loading said impact spring in response to said manually applied force, and means for restraining said plunger until said spring is loaded and thereafter releasing said plunger to impact said pusher-activating means.

3. The instrument defined in claim 2, wherein said means for restraining said plunger comprises a latch spring and an abutment against which said latch spring abuts while said impact spring is being loaded.

4. The instrument defined in claim 3, wherein said means for releasing said plunger comprises means for camming said latch spring out of abutment with said abutment when said spring is loaded.

5. The instrument defined in claim 1, wherein said pusher-activating means comprises a thrust bar slidably mounted in said main body portion and said trigger means comprises a handle pivotally mounted to said main body portion and having a lower hand-engaging portion and an upper force-transmitting portion associated with said thrust bar.

6. The instrument defined in claim 5, wherein said instrument further comprises collar means housed in said main body portion for transmitting force from said trigger means to said pusher-activating means.

7. The instrument defined in claim 1, and further comprising a nose portion and means for mounting said staple-carrying cartridge in said nose portion so that said cartridge is rotatable therewith, said pusher-activating means being housed in said nose portion and rotatable therewith.

8. The instrument defined in claim 1, wherein said instrument further comprises clutch means for preventing said pusher-activating means from activating said pusher to advance said staples in said cartridge more than once in each stapling operation.

9. The instrument defined in claim 1, wherein said pusher-activating means comprises a thrust bar slidingly mounted for reciprocative movement in said main body portion and wherein a clutch means prevents said thrust bar from returning to its initial rest position until said thrust bar has completed its forward thrust movement.

10. A manually powered surgical stapling instrument for applying sterilized staples to the disunited skin or fascia of a patient for affecting a joining of the skin or fascia, the instrument adapted to associate with a staple-carrying cartridge having anvil means at one end thereof and adapted to house a plurality of staples therein, a pusher element slidably mounted therein for advancing said staples in said cartridge, for ejecting said staples from said cartridge and for forming said staples around said anvil means, said surgical stapling instrument comprising: a main body portion; means for mounting said staple-carrying cartridge on said main body portion; pusher-activating means including a thrust bar slidably mounted in said main body portion for driving said pusher element forward to advance, eject and form said staples; trigger means for transmitting a manually applied force to said pusher-activating means to power said pusher-activating means to advance said staples, said trigger means including a handle pivotally mounted to said main body portion having a lower hand-engaging portion and an upper force-transmitting portion and collar means housed in said main body portion for transmitting force from said handle to said thrust bar, said collar means including a cylindrically-shaped body member having outwardly and radially extending flange portions at each end thereof, said upper force-transmitting portion of said trigger means being formed in the shape of a yoke and positioned around said cylindrically-shaped body member and between said flange portions of said collar means so that said collar means can rotate relative to said trigger means; and impact means powered by said trigger means for impacting said pusher-activating means and ejecting and forming said staples.

11. A manually powered surgical stapling instrument for applying sterilized staples to the disunited skin or fascia of a patient for affecting a joining of the skin or fascia, the instrument adapted to associate with a staple-carrying cartridge having anvil means at one end thereof and adapted to house a plurality of staples therein, a pusher element slidably mounted therein for advancing said staples in said cartridge, for ejecting said staples from said cartridge and for forming said staples around said anvil means, said surgical stapling instrument comprising: a main body portion; means for mounting said staple-carrying cartridge on said main body portion; pusher-activating means for driving said pusher element forward to advance, eject and form said staples; trigger means for transmitting a manually applied force to said pusher-activating means to power said pusher-activating means to advance said staples; and impact means powered by said trigger means for staples, said pusher-activating means and ejecting and forming said staple, said impact means including an impact spring, a plunger acted upon by said impact spring, means for loading said impact spring in response to said manually applied force, and means for restraining said plunger until said spring is loaded and thereafter releasing said pusher-activating means, said means for restraining said plunger including a latch spring and an abutment against which said latch spring abuts while said impact spring is being loaded.

12. The instrument defined in claim 11, wherein said means for releasing said plunger comprises means for camming said latch spring out of abutment with said abutment when said spring is loaded.

13. A manually powered surgical stapling instrument for applying sterilized staples to the disunited skin or fascia of a patient for affecting a joining of the skin or fascia, the instrument adapted to associate with a staple-carrying cartridge having anvil means at one end thereof and adapted to house a plurality of staples therein, a pusher element slidably mounted therein for advancing said staples in said cartridge, for ejecting said staples from said cartridge and for forming said staples around said anvil means, said surgical stapling instrument comprising: a main body portion; means for mounting said staple-carrying cartridge on said main body portion; pusher-activating means including a thrust bar slidably mounted in said main body portion for driving said pusher element forward to advance, eject and form said staples; trigger means for transmitting a manually applied force to said pusher-activating means to power said pusher-activating means to advance said staples, said trigger means including a handle pivotally mounted to said main body portion having a lower hand-engaging portion and an upper force-transmitting portion, collar means housed in said main body portion and associated with said upper force-transmitting portion of said handle, and a thrust tube housed in said main body portion and coupled to said collar means, said thrust tube being associated with said thrust bar for transmitting force from said handle to said thrust bar; and impact means powered by said trigger means for impacting said pusher-activating means and ejecting and forming said staples, said impact means comprises an impact spring, a plunger acted upon by said impact spring, means for loading said impact spring in response to said manually applied force, and means for restraining said plunger until said spring is loaded and thereafter releasing said plunger to impact said pusher-activating means, said means for restraining said plunger including a latch spring and an abutment against which said latch spring abuts while said impact spring is being loaded.

14. The instrument defined in claim 13, wherein said means for releasing said plunger comprises means associated with said thrust tube for camming said latch spring out of abutment with said abutment when said spring is loaded.

* * * * *